United States Patent [19]

Upmacis et al.

[11] Patent Number: 5,262,569

[45] Date of Patent: Nov. 16, 1993

[54] SALTS OF N-NITROSOPHENYLHYDROXYLAMINE

[75] Inventors: Rita K. Upmacis, North Wales; William Bauer, Jr., Huntingdon Valley, both of Pa.; Samuel F. Reed, Jr., Seabrook, Tex.

[73] Assignee: Rohm and Haas Company, Philadelphia, Pa.

[21] Appl. No.: 731,562

[22] Filed: Jul. 17, 1991

[51] Int. Cl.$^5$ ............... C07C 243/06; C07D 295/088
[52] U.S. Cl. ..................................... 564/112; 544/170
[58] Field of Search ........................... 564/112, 113

[56] References Cited

U.S. PATENT DOCUMENTS

| | | |
|---|---|---|
| 3,426,063 | 2/1969 | Gros .................. 260/666.5 |
| 4,638,079 | 1/1987 | Inskip ..................... 560/4 |
| 4,772,740 | 9/1988 | Varwig ..................... 560/4 |

FOREIGN PATENT DOCUMENTS 194016 6/1986 European Pat. Off. .
9105551 2/1991 World Int. Prop. O. .

*Primary Examiner*—Glennon H. Hollrah
*Assistant Examiner*—P. O'Sullivan
*Attorney, Agent, or Firm*—Terence P. Strobaugh

[57] ABSTRACT

Disclosed are salts of N-nitrosophenylhydroxylamine and their use as polymerization inhibitors.

9 Claims, No Drawings

SALTS OF N-NITROSOPHENYLHYDROXYLAMINE

This invention relates to salts of N-nitrosophenylhydroxylamine, solutions thereof and inhibiting polymerization therewith.

BACKGROUND OF THE INVENTION

The ammonium salt of N-nitrosophenylhydroxyamine (cupferron) is a known polymerization inhibitor but has several drawbacks including its limited solubility which makes it difficult to add to some process streams.

Other derivatives of N-nitrosophenylhydroxyamine are also known (Gros, et al., U.S. Pat. No. 3,426,063 and Varwig U.S. Pat. No. 4,772,740). Solvents must be employed to prepare usable solutions. These solvents often cause problems during use. Cupferron has limited solubility in solvents such as water and lower alcohols. Cupferron has the following limits of solubility at 25° C. in the indicated solvents: water (12%), methanol (5.5%) and isopropanol (0.38%), while it is essentially insoluble in hydrophobic solvent i.e., solvents which are immiscible with water. As a result of the limited solubilities of cupferron in the foregoing solvents, objectionably large amounts of these solvents are required in many applications where cupferron would otherwise be a desirable inhibitor.

Solutions of cupferron undergo degradation in the presence of air, as manifested by discoloration and formation of a black precipitate. Minimizing the extent and rate of degradation requires storing such solutions under an inert atmosphere such as nitrogen.

The above-mentioned deficiencies of cupferron solutions are not overcome by the salts of N-nitrosophenylhydroxylamine disclosed in the above-cited Gros patent. On the contrary, these salts of N-nitrosophenylhydroxylamine (NPHA) are unsatisfactory for use in inhibiting polymer formation in acrylic acids and acrylate esters. In the presence of such monomers, the amine salts decompose with formation of the organic aliphatic amines (e.g. ethylamine, etc.). The lower boiling amines (e.g. the $C_1$ to $C_7$ aliphatic amines) formed by decomposition of the corresponding amine salts create a substantial risk of co-distillation thereof with the acrylic acid or acrylate ester monomers being purified by distillation and resulting discoloration of polymers prepared from the monomers, such as, for example, poly(acrylic acid), poly(methyl methacrylate) and poly(ethyl acrylate). The higher boiling amines (e.g. the $C_8$-$C_{20}$ aliphatic amines) formed upon decomposition of the corresponding amine salts are so immiscible with water that such salts are not entirely satisfactory for addition to water-containing acrylic acid systems.

Accordingly there is a need for a salt of NPHA which can be added to acrylic acid and acrylate ester systems and is effective for inhibiting undesired formation of polymer in such systems.

DESCRIPTION OF THE INVENTION

Compounds have now been found which substantially fulfill the above-mentioned need. There is no risk of co-distillation of the amines formed upon decomposition of these corresponding amine salts of NPHA with the acrylic acid or acrylate ester monomers being purified by distillation.

Generally stated, in one aspect of the present invention there is provided novel salts of NPHA.

In yet another aspect, this invention provides a method for inhibiting formation of undesired polymer from monomers, especially acrylic acids, which comprises adding thereto the novel salts of NPHA in an amount effective for inhibiting the formation of such polymer.

DETAILED DESCRIPTION OF THE INVENTION AND THE MANNER AND PROCESS OF MAKING AND USING IT

The (stoichiometric or non-stoichiometric) salts of NPHA comprising a mono-, di- or higher substituted basic salt of our organic amine are represented in the neutral form (for convenience) by the following formula:

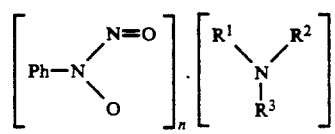

wherein n is an integer of from one to the number of basic nitrogens in the amine and preferably is 1 to 3; $R^1$ is hydrogen, alkyl, for example lower alkyl of from 1 to 5 carbon atoms such as methyl, ethyl, propyl, butyl, pentyl and the like, or hydroxyalkyl, for example, hydroxy lower alkyl of from 1 to 5 carbon atoms, such as, hydroxymethyl, hydroxyethyl, hydroxypropyl, hydroxybutyl, hydroxypentyl, and the like; hydroxy alkoxy alkyl, for example, hydroxy alkoxy lower alkyl, such as hydroxyethoxy ethyl or hydroxy alkylamino alkyl, for example hydroxy lower alkylamino lower alkyl, such as, hydroxyethylaminoethyl and the like;

$R^2$ is hydrogen; alkyl as defined above; aminoalkyl, for example amino lower alkyl of from 1 to 10 carbon atoms such as aminomethyl, aminoethyl, aminopropyl, aminobutyl, aminopentyl, aminohexyl, aminoheptyl, aminooctyl, aminononyl, aminodecyl and the like, or aminophenyl;

$R^3$ is alkyl as defined above; aminoalkyl as defined above; or $R^2$ and $R^3$ may be joined together with the nitrogen atom to which they are attached to form a morpholino ring with the proviso that when $R^1$ is hydroxyalkyl, $R^2$ and $R^3$ are joined together with the nitrogen atom to which they are attached to form a substituted or unsubstituted, saturated or unsaturated, heterocyclic ring. For example, a heterocyclic ring of from 2 to 8 carbon atoms and from 1 to 3 hetero atoms selected from nitrogen, or oxygen or both, such as, morpholino, pyrrolidinyl, pyrrolyl, imidazolyl, pyrazolyl, piperidinyl, pyridinyl, pyridazinyl, pyrazinyl, piperazinyl, triazolyl, triazinyl, indolyl and the like where the substituent is alkyl, for example, lower alkyl of from 1 to 5 carbon atoms or hydroxyalkyl, for example, hydroxy lower alkyl, such as; hydroxymethyl, hydroxyethyl, hydroxypropyl, hydroxybutyl, hydroxypentyl and the like. 1, 2 or 3 of the available nitrogen atoms to form mono-, di- or higher substituted salts.

It is not required that the salts be stoichiometric compounds, but only that the number of basic nitrogens is at least equal to the number of NPHA moieties present.

The salts of NPHA of this invention may be monosubstituted, disubstituted, trisubstituted or even higher depending on the particular salt selected.

Some examples of the salts include the following where $A^\ominus$ is the symbol for

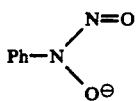

1. Diethylene triamine
Monosubstituted

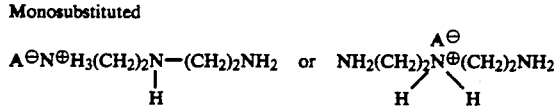

Disubstituted

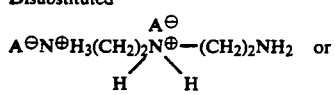

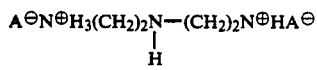

Trisubstituted

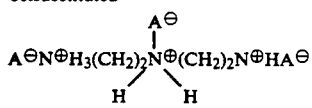

2. Ethylene Diamine
Monosubstituted
$A^\ominus N^\oplus H_3CH_2CH_2NH_2$

Disubstituted
$A^\ominus N^\oplus H_3CH_2CH_2N^\oplus H_3A^\ominus$

3. Meta-phenylene diamine
Monosubstituted

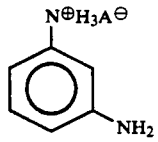

Disubstituted

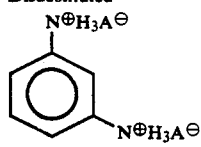

4. 4-(2-hydroxyethyl)morpholine

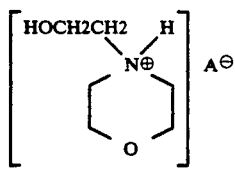

5. Tributylamine

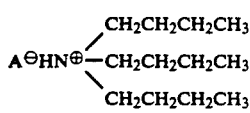

6. 1,4-Butylene Diamine
Monosubstituted
$A^\ominus N^\oplus H_3CH_2CH_2CH_2CH_2NH_2$ Disubstituted
$A^\ominus N^\oplus H_3CH_2CH_2CH_2CH_2N^\oplus H_3A^\ominus$ 7. 3,3'-Iminobispropylamine
Monosubstituted

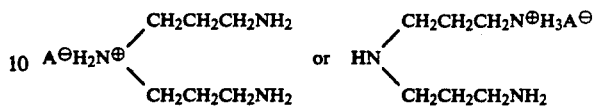

Disubstituted

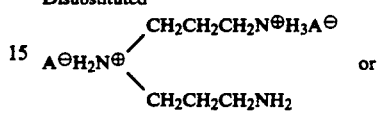

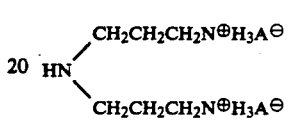

Other amines which may be used include propylene diamine, dibutylene triamine, tetraethyl pentamine, tetrabutyl pentamine, tetraethylene diamine, tetrabutylene diamine, triethyl amine, pentaethylene hexamine, hexamethylene tetramine, 4-ethylmorpholine, 4-butyl-morpholine, o, or p-aminoanilines.

The salts of NPHA employed in this invention can be prepared by (i) reacting an equimolar ratio of the amine and cupferron in a solvent that can be removed by subsequent evaporation of the solvent to form a dry salt, and (ii) reacting the amine with cupferron in an excess of the amine as the solvent, preferably sparging the reaction system with nitrogen or other inert gases to aid in removing the ammonia which evolves in the course of the reaction.

In general, where a solvent other than excess amine is desired in the synthesis of these salts of NPHA, polar organic solvents capable of dissolving amines may be used. Alcohols are preferred, and isopropanol is especially preferred for use as the reaction solvent. Preferably, cupferron is added to the reaction solvent and thereafter the amine is added to the rest of the solution with stirring. In general, cupferron is added in an approximately stoichiometric amount, i.e., in an amount such that a total of approximately one mole of cupferron is added per mole of amine. However, if excess amine is desired as the solvent, cupferron may be added in an amount less than stoichiometric. Preferably, equal parts by weight of the amine and cupferron are employed. The reaction may be carried out under any suitable conditions, including a temperature of, for example, about 50° and atmospheric pressure. The time required to complete the reaction is dependent upon the amine employed, reaction temperature, and the relative amounts of reactants. The dry salt can be recovered from the alcohol solvent using well-known recovery methods. Recovery may be effected, for example, by cooling the reaction mixture to about 0° C. to crystallize the salt of NPHA.

The salts of NPHA can be stored in the atmosphere over long periods of time without degradation in the following ways (i) as the dry salt of NPHA, (ii) the salt of NPHA in excess amine or (iii) in solutions containing the salt of NPHA in a polar solvent such as water or an alcohol such as isopropanol and the like. No discoloration or formation of black solids or precipitate is observed over a period of months.

Another part of this invention involves a method for inhibiting formation of undesired polymer from an ethylenically unsaturated monomer selected from polymerizable ethylenically unsaturated acids, esters or mixtures thereof in a distillation unit which comprises adding an effective amount of the salt of NPHA to the unit.

The salts of NPHA have been found to be effective inhibitors of undesired polymerization such as thermal polymerization and popcorn polymer formation in ethylenically unsaturated acids and esters, such as acrylic acids and esters thereof. They are effective for inhibiting undesired polymerization in both liquid phases and vapor phases. That is, inhibition can be effected in liquid phases of such monomers, as well as in the vapor spaces above such liquid phases.

As used herein, the term "acrylic acids" includes substituted and unsubstituted acrylic acid, e.g. acrylic acid per se, methacrylic acid and the like. Monomeric esters of such acids include, for example, esters thereof with a lower alkanol having from 1 to about 8 carbon atoms, such as the methyl, ethyl, isopropyl, butyl and octyl (e.g. 2-ethylhexyl) alcohols.

The various inhibited monomer solutions may be prepared by simply admixing at any suitable temperature (e.g. about 20° C. to 25° C.) one or more of the new salt compounds with the monomer to be inhibited.

It is understood that the salts of NPHA may, if desired, be introduced into, or otherwise admixed with, monomers or monomer containing systems to be inhibited. The salts may be added as is or in solution, for example, an aqueous solution or an alcohol solution.

The salts of NPHA may be admixed with an all-monomer system or other monomer-containing system employing any effective amount of the NPHA salt. Expressed on the basis of the amount of NPHA in the salts of NPHA, effective amounts are generally in the range of from about 20 to about 1000 parts per million (ppm) of the monomer. It has been found that addition of such amounts to monomers or monomer-containing systems such as the acrylic acids and esters thereof effectively inhibits thermal polymerization of such monomers, while at the same time effectively inhibits formation of popcorn polymer. Advantageously, the inhibiting effects achieved are observed in both the liquid and the vapor phase.

The % conversion of cupferron to other salts of NPHA is extremely important. If the reaction is incomplete (residual amounts of cupferron remain in the reaction mix) then poorer inhibition is observed.

Practice of the present invention is illustrated by the following examples, which are given by way of illustration and not by way of limitation. As indicated above, all amounts throughout this disclosure are by weight unless otherwise indicated.

Preparation of The Salts of
N-Nitrosophenylhydroxylamine

The salts of N-nitrosophenylhydroxylamine can be prepared as both dry (Preparation I, below) and solution forms in excess amine (Preparation II, below). The two Preparations are similar but differ in the following ways:

(i) 1:1 molar ratios of cupferron:amine are used for the preparation of the dry salt (however, if the amine has two amino functional groups, it is possible to prepare the 2 cupferron:1 amine molar ratio salt and so forth), (ii) the dry salt is prepared in the presence of isopropanol which is not required for the preparation of the solution form, and (iii) 50%:50% (w/w) ratios of cupferron:amine are used for the preparation of the solution form of the salts. (Since the molecular weight of cupferron is higher than that of any of the amines used in the following examples, the amine is always present in excess). In all cases, with the exception of meta-phenylene diamine, the amines used were liquids and thus, the presence of a solvent was not necessary in the preparation of the solution forms of these salts.

PREPARATION I

Preparation of an Amine Salt of
N-Nitrosophenylhydroxylamine Using 1:1 molar ratios
of Cupferron and Amine Cupferron (5 g, 0.0322 moles) and isopropanol (15 ml) are added to a 25 ml three neck round bottom flask. [Note: in the preparation of the metaphenylene diamine salt of NPHA, MeOH was used as the solvent and not iPrOH]. Stirring is begun and the system sparged with nitrogen (to remove ammonia) and the amine of choice (0.0322 moles) is added to the flask, via a pre-weighed syringe, through a septum on one of the necks on the flask. The syringe is then reweighed to determine the exact amount of amine used. Once the amine has been added, the flask is heated to 50° C. and held at this temperature for about 2 hr. After heating for 2 hr., the oil bath is lowered and the flask allowed to cool under nitrogen. If necessary, the reaction mixture can be heated further until the desired conversion has been achieved (See Note b, Table I). When a satisfactory conversion has been achieved, the mixture is allowed to stand, undisturbed under nitrogen to allow the salt to crystallize. The solid is removed from the flask, vacuum filtered, washed with hexane and placed in a tared beaker to dry in a vacuum oven. The salt is then weighed and stored in a bottle until further use.

PREPARATION II

Preparation of an Amine Salt of
N-Nitrosophenylhydroxylamine in Excess Amine
(Solution Form) Using 50:50 (w/w) Cupferron and
Amine Cupferron (~5 g) is added to a 25 ml. three neck round bottom flask to the flask, via a pre-weighted syringe, through a septum on one of the and held at this temperature for about 2 hr. After heating for 2 hr., the oil bath is lowered and the flask allowed to cool under nitrogen. If necessary, the reaction mixture can be heated further until the desired conversion has been achieved. When a satisfactory conversion has been achieved, (See Note b, Table I) the mixture is removed from the flask, weighed and stored until further use.

TABLE I

Preparation of Amine Salts of N-Nitrosophenylhydroxylamine

| Example | Amine | Cupferron:Amine Ratio[a] | % Conversion[b] | Remarks |
|---|---|---|---|---|
| 1 | Diethylene Triamine | 2:1 (molar) | 72.66 | 2 hr. reaction time. |
|   |   | 3:1 (molar) | 48.56 | 2 hr. reaction time. |
|   |   | 50:50 (w/w) | 81.28 | measured after 6.7 hr. |
|   |   |   | 93.62 | 33.7 hr. total reaction time. |
| 2 | Ethylene Diamine | 1:1 (molar) | 82.19 | 2 hr. reaction time. |
|   |   | 2:1 (molar) | 43.88 | 2 hr. reaction time. |
|   |   | 50:50 (w/w) | 83.54 | 2 hr. reaction time. |
|   |   | 50:50 (w/w) | 91.2 | measured after 4.3 hr. |
|   |   |   | 94.23 | 8.5 hr. total reaction time. |
| 3 | m-Phenylene Diamine | 50:50 (w/w) |   | Prepared in MeOH. |
|   |   |   | 3.9 | 2.5 hr. total reaction time |
|   |   |   | 17.87 | 9 hr. total reaction time. |
|   |   |   | 48.20 | 31.3 hr. total reaction time. |
|   |   |   | 63.21 | 49.3 hr. total reaction time. |
|   |   |   | 96.70 | 150 hr. total reaction time. |
| 4 | 4-(2-Hydroxyethyl)morpholine) | 1:1 (molar) | 10.25 | 4.5 hr. reaction time. |
|   |   |   | 62.23 | 105.5 hr. total reaction time. |
|   |   |   | 93.53 | 171 hr. total reaction time. |
|   |   | 50:50 (w/w) | 7.30 | 4.5 hr. reaction time |
|   |   |   | 46.00 | 104 hr. total reaction time. |
|   |   |   | 53.00 | 201 hr. total reaction time. |
| 5 | Tributyl Amine | 1:1 (molar) | 25.18 | 5.5 hr. reaction time. |
|   |   |   | 70.32 | 76.5 hr. total reaction time. |
|   |   |   | 97.48 | 174.5 hr. total reaction time. |
|   |   | 50:50 (w/w) | 5.80 | 5.5 hr. reaction time. |
|   |   |   | 24.14 | 53 hr. total reaction time. |
| 6 | 3,3'-Iminobispropylamine | 3:1 (molar) | 84.53 | 72 hr. total reaction time. |
|   |   |   | 87.23 | 98 hr. total reaction time. |
|   |   |   | 89.75 | 171 hr. total reaction time. |
|   |   | 50:50 (w/w) | 89.34 | 4 hr. reaction time. |
|   |   |   | 99.57 | 28 hr. total reaction time. |

Notes:
[a]The cupferron:Amine Ratio is given either as a molar ratio (in cases where the dry salt preparation, i.e. Prep. I. was followed), or as a % weight ratio (in cases where the salt was prepared in excess amine, i.e. Prep. II).
[b]The % conversion is calculated by measuring the amount of NH₃ evolved. This is done by titrating the solution in the scrubber with a sodium hydroxide solution (0.5N) using phenolphthalein as an indicator.

EXAMPLE 7

Evaluation

The method of evaluation of the inhibitors involves monitoring the inhibiting performance of the amine salts of NPHA under distillation conditions. The distillation apparatus consists of a 1L five neck distillation flask surmounted by two 5-tray Oldershaw column sections. A standard magnetically controlled reflux distillation head containing a finger-type condensor and a thermometer joint is connected to the top of the Oldershaw column.

Before the start of the experiment, an initial charge of acrylic acid (AA) (500 g) containing 4-methoxyphenol (MEHQ; 200 ppm), phenothiazine (PTZ; 600 ppm) and hydroquinone (HQ; 600 ppm) is made to the flask. During the distillation, AA (inhibited with 200 ppm MEHQ) is fed to the flask at a rate of 90 cc/hr. Dry air is also fed to the flask below the liquid level at a rate of 20 cc/min. A reflux ratio of 4 (i.e. 20% collected as distillate and 80% refluxed) is maintained throughout the distillation experiment which lasts 4 hr. A bottoms bleed of 40 cc/hr is removed manually, 20 cc every 30 min.

Liquid phase inhibitor solution (1.0 wt. % each of PTZ and HQ in acrylic acid) is fed to the condensor at the top of the column at a rate of 20 cc/hr in each experiment. This is to ensure that (i) the distillate samples are adequately inhibited and that (ii) the experiment does not fail prematurely due to inadequate liquid phase inhibition on the trays in the column of the distillation apparatus.

The salt of NPHA is delivered to the flask as a solution in AA (unless water is indicated) at 10 cc/hr. The amount of inhibitor added is expressed as ppm active ingredient (as NPHA) based on liquid volume in the flask.

During the 4 hr experiment, the distillation apparatus is monitored for any visual evidence of polymer in the distillation head. The method of presenting results involves counting specks of polymer in the distillation head, where no liquid splashing occurs and where condensation of vapor is more likely.

The results for the salts of NPHA and also for some standards (including cupferron and the ethanolamine salt of NPHA) are given in Table II. Unless otherwise indicated, the numbers given in Table II represent the number of specks of polymer≦1 mm in size.

EXAMPLE 8

Study of Codistillation of Amines with Acrylic Acid

The amines employed do not codistill with acrylic acid as shown by an HPLC study conducted on the distillate of an ethylene diamine salt which indicated 0 ppm of ethylene diamine.

TABLE II

Evaluation of Amine Salts of
N-Nitrosophenylhydroxylamine

| Salt | ppm NPHA | Number of Specks of Polymer in the Distribution Head |
|---|---|---|
| Diethylene Triamine* | 26 | 0 |
| Ethylene Diamine | 39 | 3 |
| 3,3'-Iminobispropylamine | 26 | 2 |
| Ethylene Diamine | 26 | 2, 6, 3, 2, 5 |
| Ethylene Diamine* | 26 | 4 |
| meta-Phenylene Diamine# | 26 | 5 |
| Tributylamine | 26 | 9 |
| 4-(2-Hydroxyethyl) morpholine | 26 | 12 |
| Diethylene Triamine | 26 | 17$^a$, 11$^a$ |
| Butyl Diamine | 26 | 23$^b$ |
| Diethylene Triamine | 32 | 6 |
| STANDARDS | | |
| Ethanolamine* | 26 | 4$^a$ |
| Ethanolamine | 26 | 14, 9, 35 |
| " | 25 | 17 |
| " | 11 | 20$^c$ |
| No Vapor Phase Inhibitor | — | 15$^a$, 36 |
| Cupferron | 29 | 47, 28, 14 |

Notes:
$^a$Includes 1-3 × 2 mm specks.
$^b$Includes 1 × 4 mm ball of polymer.
$^c$Includes 2 × >5 mm balls of polymer.
Based on liquid volume in the distillation flask.
Each number represents a result from a single experiment.
*NPHA salt delivered in water.
Synthesis involved preparation in MeOH.

EXAMPLE 9

Percent Conversion of Cupferron vs. Activity

The following shows the decrease in activity when there is a large amount of cupferron still remaining in the reaction mixture.

TABLE III

Percent Conversion of Cupferron vs. Activity

| Salt of NPHA | % Conv. | ppm NPHA | Number of Specks of Polymer in the Distillation Head |
|---|---|---|---|
| Ethylene Diamine | 75% | 26 | 14(a) |
| Ethylene Diamine | 75% | 26 | 12(b) |
| Ethylene Diamine | 75% | 26 | 10 |
| Ethylene Diamine | 92% | 26 | 3 |
| Ethylene Diamine | 92% | 26 | 2 |
| Ethylene Diamine | 92% | 26 | 5 |

(a) includes >3 × 2 mm specks of polymer.
(b) includes 1 × 5 mm ball of polymer.
Based liquid volume in the distillation flask.

EXAMPLE 10

Physical Properties

The Table below shows viscosities of different concentrations of aqueous solutions of the ethylene diamine (EDA) salt of NPHA at temperatures of 30° C. and 7° C. For comparison, water has a viscosity of 0.7975 cp and 1.428 cp at 30° C. and 7° C., respectively. Ethylene Glycol has a viscosity of 19.9 cp at 20° C.

TABLE IV

Viscosities of Different Concentrations
of Aqueous Solutions of the Ethylene Diamine
Salt of NPHA

| Salt of NPHA (wt. %) | Other Components (wt. %) | Viscosity (cp) at 30° C. | Viscosity (cp) at 7° C. |
|---|---|---|---|
| 40% EDA/NPHA | 20% EDA 40% Water | 10.60 | 38.61 |
| 19% EDA/NPHA | 48% EDA 33% Water | 11.48 | 46.57 |
| 20% EDA/NPHA | 10% EDA 70% Water | 5.01 | 11.56 |
| 24% EDA/NPHA | 13% EDA 63% Water | 2.90 | 8.13 |

The viscosities of the above solutions indicate that they could be easily handled under plant conditions at different temperatures.

In addition to the inhibitor solution having a manageable viscosity, it is also important that such a solution not freeze during cold weather which could cause inhibition problems. The freezing point of a solution comprising 20% ethylene diamine salt of NPHA, 10% ethylene diamine and 70% water was measured to be between −12° C. and −17° C.

Aqueous solutions of the ethylene diamine salt have been monitored for a period of 3 months, and no black solids or decomposition products have been observed during this time period.

What is claimed is:

1. A salt of N-nitrosophenylhydroxylamine (NPHA) and an amine, expressed in the neutral form as Formula I:

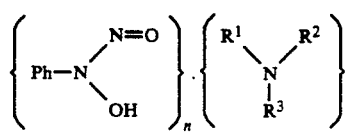

wherein n is an integer of from one to the number of basic nitrogens in the amine; $R^1$ is hydrogen or $C_1$–$C_5$ alkyl; $R^2$ is hydrogen, $C_1$–$C_5$ alkyl, or $C_1$–$C_{10}$ aminoalkyl; and $R^3$ is $C_1-C_5$ alkyl or $C_1-C_{10}$ aminoalkyl; provided that:

a. if $R^1$ is hydrogen then $R^2$ and $R^3$ cannot both be $C_1-C_5$ alkyl, b. if $R^2$ is hydrogen then $R^1$ and $R^3$ cannot both be $C_1-C_5$ alkyl, and, c. If $R^1$ and $R^2$ are both hydrogen then $R^3$ cannot be $C_1-C_5$ alkyl.

2. The salt of claim 1 wherein $R^1$ is hydrogen or $C_1-C_5$ alkyl; $R^2$ is hydrogen, $C_1-C_5$ alkyl or $C_1-C_5$ amino alkyl; and $R^3$ is $C_1-C_5$ alkyl or $C_1-C_5$ aminoalkyl.

3. The salt of claim 2 wherein $R^1$ is hydrogen or butyl; $R^2$ is hydrogen, butyl or aminoethyl; and $R^3$ is butyl or aminoethyl.

4. The salt of claim 3 wherein $R^1$ is hydrogen; and $R^2$ and $R^3$ are aminoethyl.

5. The salt of claim 3 wherein $R^1$ and $R^2$ are hydrogen and $R^3$ is aminoethyl.

6. The salt of claim 3 wherein $R^1$, $R^2$ and $R^3$ are butyl.

7. The salt of claim 2 wherein $R^1$ is hydrogen; $R^2$ is hydrogen, aminoethyl, or aminopropyl; and $R^3$ is aminoethyl, aminopropyl, or aminobutyl.

8. The salt of claim 2 wherein $R^1$ and $R^2$ are hydrogen.

9. The salt of claim 2 wherein $R^1$ is hydrogen and $R^2$ and $R^3$ are 3-aminopropyl.

* * * * *